United States Patent [19]

Bunning et al.

[11] Patent Number: 4,999,452

[45] Date of Patent: Mar. 12, 1991

[54] PROCESS FOR PRODUCING ACRYLIC ESTER

[75] Inventors: Donald L. Bunning, South Charleston; William G. Etzkorn, Cross Lanes; William M. Haydon, South Charleston; Gordon G. Harkreader, Charleston; Jonathan J. Kurland, Charleston; Wai C. Liu, Charleston; Ernesto Vera-Castaneda, Charleston, all of W. Va.

[73] Assignee: Union Carbide Chemicals and Plastics Company Inc., Danbury, Conn.

[21] Appl. No.: 351,479

[22] Filed: May 15, 1989

[51] Int. Cl.$^5$ .............................................. C07C 67/00
[52] U.S. Cl. ..................................... 560/208; 562/600
[58] Field of Search ........................ 560/208; 562/600

[56] References Cited

U.S. PATENT DOCUMENTS

| | | |
|---|---|---|
| 3,717,675 | 2/1973 | Sennewald et al. . |
| 3,868,417 | 2/1975 | Duembogen et al. . |
| 3,875,212 | 4/1975 | Ohrui et al. . |
| 3,914,290 | 10/1975 | Otsuki et al. . |
| 3,926,744 | 12/1975 | Noll et al. . |
| 4,040,913 | 8/1977 | Clovis et al. . |
| 4,049,577 | 9/1977 | Childress et al. . |
| 4,110,370 | 8/1978 | Engelbach et al. . |
| 4,156,633 | 5/1979 | Horlenko et al. . |
| 4,166,774 | 9/1979 | Smith . |
| 4,199,410 | 4/1980 | Ohrui et al. . |
| 4,280,010 | 7/1981 | Erpenbach et al. . |
| 4,317,926 | 2/1982 | Sato et al. . |
| 4,442,308 | 4/1984 | Arntz et al. . |
| 4,453,006 | 6/1984 | Shaw et al. . |
| 4,554,054 | 11/1985 | Coyle ................................... 203/15 |
| 4,599,144 | 7/1986 | Baleiko et al. . |

FOREIGN PATENT DOCUMENTS

| | | |
|---|---|---|
| 1193282 | 9/1985 | Canada . |
| 0009545 | 4/1980 | European Pat. Off. . |
| 0253409 | 1/1988 | European Pat. Off. . |
| 00257565 | 3/1988 | European Pat. Off. . |

*Primary Examiner*—Paul J. Killos
*Attorney, Agent, or Firm*—Reynold J. Finnegan

[57] ABSTRACT

A process for producing acrylic ester by the catalytic esterification of a crude liquid stream of enriched acrylic acid recovered by the partial condensation of the reaction gas effluent from the catalytic oxidation of propylene and/or acrolein. The partial condensation allows a significant proportion of volatile aldehydes and water to pass through the first recovery stage to a second stage for conventional recovery, along with uncondensed acrylic acid vapors and the remainder of the uncondensed reaction gases.

15 Claims, No Drawings

PROCESS FOR PRODUCING ACRYLIC ESTER

BACKGROUND OF THE INVENTION

1. Field of the Invention

The present invention relates to processes for producing acrylic esters by the catalytic esterification of acrylic acid. More specifically, this invention describes an improved process for recovering a crude enriched acrylic acid fraction from the gas mixture produced from the oxidation of propylene and/or acrolein and to using the same in processes for producing acrylic esters.

2. Description of the Related Art

The catalytic oxidation of the gaseous phases of propylene or acrolein are well-known, important commercial processes for respectively producing acrolein and acrylic acid. The processes involve reacting propylene and/or acrolein in the presence of gases containing molecular oxygen (usually in the form of air) by contacting solid metal oxide catalysts at elevated temperatures.

Recently, propylene has been oxidized to acrylic acid using a reaction scheme involving a two-stage reactor wherein propylene is converted to acrolein in the presence of a catalyst in the first reactor stage. Generally, the catalyst in the first reactor stage is a solid mixed metal oxide made from various combinations of oxides of metals such as molybdenum, bismuth, tungsten, antimony, iron, phosphorous, cobalt and nickel.

The acrolein produced in the first stage reaction can then be recovered (separated) or it can be directed without separation to the second reactor stage operating in series with the first reactor stage. The second reactor stage oxidizes the acrolein to acrylic acid using catalysts which are generally solid mixed metal oxides made from various combinations of oxides of molybdenum, vanadium, tungsten, niobium, tantalum, antimony, chromium and copper.

The reaction gas mixture from the second stage oxidation reaction generally has a temperature ranging from about 250° C. to about 450° C. and essentially consists of acrylic acid product together with propylene, acrolein, oxygen, and gaseous diluents such as inert gases and steam.

Crude acrylic acid can be recovered from the hot reaction gases by low temperature cooling of the gases indirectly through heat exchangers, and/or directly through quenching and/or scrubbing the hot gases with water, pre-cooled reaction products, and/or other suitable solvents. Typically, the reaction gas effluent from the acrylic acid production is quenched to obtain a first liquid solution of crude acrylic acid and a gas stream. The gas stream is scrubbed with water in a column or absorber to yield a second aqueous solution of crude acrylic acid which is generally mixed with the first solution of crude acrylic acid. The combined aqueous crude acrylic acid solution is then preferably extensively purified to obtain ester grade or glacial acrylic acid.

Refining of crude acrylic acid generally involves a number of recovery and purifying procedures such as extraction or entrainment with various solvents. For example, in general, the refining may include co-extracting acrylic acid and acetic acid with an organic solvent, removing the solvent and water in a distillation column, and removing the acetic acid in an additional distillation column. This acrylic acid can then be further purified in still other distillation columns to make glacial acrylic acid or ester grade acrylic acid suitable for use with alcohol in an esterification reactor to form desired esters.

Typical acrylic acid recovery and refining schemes include, e.g., (i) quenching and scrubbing the gaseous reactor effluent with crude product and water to recover the crude acrylic acid, (ii) extracting acrylic acid with an organic solvent, (iii) removal of the organic solvent and water via distillation, (iv) removal of acetic acid at the overhead of another distillation column, and (v) recovering ester grade acrylic acid and/or recovering the glacial acrylic acid via distillation. Phenothiazine may be fed to all columns to prevent polymerization. However, by going through the numerous various refining schemes, significant portions (on the order of 5 percent) of the acrylic acid may be lost, e.g., by dimerization.

The prior art teaches various methods for recovering acrylic acid from the hot reaction gases. For example, U.S. Pat. No. 3,926,744 describes a technique for the sequentially recovering acrylic acid and acrolein from a gas mixture resulting from the catalytic gas phase oxidation of propylene or acrolein by washing the gas mixture with a washing liquid in which the acrylic acid dissolves at about 60° C. to 120° C. and then washing the gas mixture with a washing liquid at temperatures between 0° C. and 30° C., in which the acrolein dissolves.

U.S. Pat. No. 3,717,675 shows a process for isolating acrylic acid from the reaction gases obtained by the oxidation of propylene or acrolein, wherein hot reaction gases having a temperature of 300° C. to 600° C. are indirectly pre-cooled using a heat exchanger to a temperature of 100° C. to 200° C. The pre-cooled gases are directly scrubbed with 10° C. to 50° C. water to further cool them down to 30° C. to 90° C. The resulting 10 to 45 percent aqueous acrylic acid solution is then heated up to 100° C. to 120° C. to expel residual acrolein therefrom.

European Patent Application Publication No. 0,009,545 relates to a process for the recovery of acrylic acid from gaseous acrolein oxidation reactor effluent. The recovery steps include first quenching the gaseous reactor effluent with quench liquid in order to obtain a first liquid stream and a first vapor stream, both of which contain acrylic acid. The first vapor stream is then indirectly cooled to form a second liquid stream and a second vapor stream. The second liquid stream contains acrylic acid and is recycled for use as the quench liquid of the first step. If desired, the second gas stream may be water-scrubbed to form a third vapor stream which is removed overhead and a third liquid stream, the latter of which contains acrylic acid and is removed from the bottoms and combined with the first vapor stream.

Thus, prior art recovery methods are in general directed to maximizing the recovery of acrylic acid, which is then generally extensively refined to obtain purified acrylic acid solution suitable for use in producing acrylic ester. Typically, acrylic ester is produced from acrylic acid using a direct esterification process.

In the direct esterification process for producing acrylic esters, one mole of alcohol reacts with one mole of acrylic acid in the presence of acid catalyst such as sulfuric or sulfonic acid to produce one mole of acrylic ester and one mole of water. The alcohol can be any primary alcohol, in particular, ethanol, butanol and 2-ethylhexyl alcohol can be used to produce their corresponding acrylic esters.

Since the direct esterification reaction is a reversible reaction, water is continuously removed in the form of a water/alcohol/ester azeotrope or an azeotrope with added water entrainer to drive the reaction to completion. High water concentration in the acrylic acid esterification reactor feed, or in the combined alcohol/acrylic acid esterification reactor feed will affect the esterification rate unless extra measures are employed to remove the additional water.

The U.S. Pat. application Ser. Nos. 281,887 and 239,710 are respectively equivalent to European Patent Office publications Nos. 0,257,565 and 0,253,409.

Additionally, steam diluent is generally used in the starting reactant gas mixture for the catalytic oxidation of propylene or acrolein in order to divert the reaction mixture from the explosive limit, to help disperse the heat of reaction and to assist in reaction selectivity. Although much of the prior art has regarded the use of steam diluent as being highly preferable or essential, it naturally becomes a fraction of the acrylic acid product and becomes a burdensome wastewater load after product recovery steps.

Various methods have been made to reduce steam content in the reactant gases; references such as U.S. Pat. Nos. 4,442,308, 4,456,006, and 4,049,577 either teach the use of other inert gases or recycle gases as diluents. The inert diluent gas is normally composed of nitrogen, carbon dioxide, methane, ethane, propane or steam. However, any other inert gas can be included. Particularly preferred processes are based in part on copending U.S. Pat. applications Ser. Nos. 281,887, filed Dec. 8, 1988 (which is a continuation of Ser. No. 173,033, which is a continuation of Ser. No. 898,491, filed Aug. 21, 1986) and 239,710, filed Sept. 2, 1988 (which is a continuation of Ser. No. 886,562, filed July 17, 1986) of Union Carbide Corporation which describe the use of inert diluent gases. The U.S. Pat. applications Ser. Nos. 281,887 and 239,710 are respectively equivalent to European Patent Office publications Nos. 0,257,565 and 0,253,409.

Furthermore, when the steam diluent content of the gas mixture is reduced or eliminated through the use of other inert gas diluents, the amount of water in the enriched acrylic acid recovered in the first stage partial recovery is also significantly reduced. Thus, it is important to minimize the presence of steam in the reactant gases in order to accomplish the recovery of an enriched acrylic acid fraction having both significantly reduced amounts of impurities and water.

SUMMARY OF THE INVENTION

It is an object of the present invention to provide a process for producing acrylic esters by utilizing a crude enriched acrylic acid obtained via a simple partial recovery step thereby eliminating or greatly minimizing the conventional refining normally employed in providing an ester grade acrylic acid.

The present invention comprises a staged acrylic acid recovery system wherein the acrylic acid is only partially condensed in the first (quench) stage. The operating parameters of the first stage of acrylic acid recovery are regulated such that a significant proportion of the acrylic acid vapors in the reaction gas stream are not condensed and recovered in that stage, but rather pass uncondensed to a second recovery stage.

The present inventors have discovered that by operating under conditions which only partially recover the acrylic acid content of the reaction gas stream, most of the light impurities, such as formaldehyde and acrolein, and a relatively large amount of water pass uncondensed into the second recovery stage along with the remaining uncondensed acrylic acid. Accordingly, the acrylic acid recovered in this first stage (referred to as "enriched acrylic acid") of this invention is considerably more concentrated and has fewer impurities than the crude acrylic acid typically recovered using previous techniques.

Thus, one of the advantages of the present invention is that the enriched acrylic acid recovered in the first stage partial recovery features a purity such that this partially recovered acrylic acid fraction may be fed directly to an esterification reactor without being subjected to purification or refining. In particular, the esters prepared from the enriched acrylic acid obtained by the process of the present invention have been found to be of generally comparable quality to those prepared using ester grade acrylic acid as the esterification reactor feed.

One major advantage of the subject invention in using this crude enriched acrylic acid is that it allows the expansion of acrylic ester capacity in an existing plant without the need for expanding acrylic acid refining facilities. Thus, a significant reduction in the capital costs can be realized. In addition, efficiency losses of the acrylic acid produced by the oxidation of acrolein during the recovery and refining processes which are otherwise necessary are eliminated.

In addition, through partial recovery, a relatively high proportion of water in the reaction gas effluent is passed uncondensed to the second stage acrylic acid recovery, and because the present invention allows the omission of water scrubbing, the enriched acrylic acid which is obtained has even less water content than it otherwise might.

The method of the present invention is particularly advantageous when utilized in conjunction with a process for producing acrylic acid by propylene or acrolein oxidation with inert gases other than steam as diluents. That is to say, employing the present process in conjunction with an anhydrous diluent system in the acrylic acid reactor minimizes the water content of the reaction gas mixture so that an enriched acrylic acid stream featuring a purity and concentration which is particularly suitable for being directly fed to an esterification reactor for producing acrylic esters is recovered.

Of course, when the above-mentioned anhydrous diluent system is utilized during the oxidation process, it is especially preferred that the recovery steps also do not involve the use of aqueous media. For instance, if the reactor gas effluent is to be quenched, it should be quenched with organic materials. One such preferred organic material can be provided by cooled, crude acrolein oxidation reaction product.

In general, acrylic acid is typically recovered using methods such as direct condensation via heat exchangers, falling film coolers, adsorption/scrubbing techniques, and the like. Pursuant to the invented process, the reaction gas mixture from the oxidation reactor is treated in a first recovery stage under cooling conditions sufficient only to partially condense the acrylic acid content of the gas mixture. This partial recovery can be accomplished by regulating various parameters of a suitable conventional technique.

Those skilled in the art will appreciate that the extent of acrylic acid recovery can be regulated by individually or jointly manipulating parameters such as scrubber operating pressure and temperature, the quenching liquid temperatures and flow rates, and the scrubber overhead and base temperatures. In this regard, the extent of acrylic acid recovery will decrease with increased oxidation effluent temperature and/or flow rate. In contrast, acrylic acid recovery will, of course, increase with decreased oxidation stage effluent gas temperature and/or flow rate. Additionally, acrylic acid recovery will decrease as the first condensation stage outputs materials (gases and liquids) with increased temperature and/or flow 10 rate and, of course, acrylic acid recovery increases in the first condensation stage output with decreased temperature and/or flow rate.

DETAILED DESCRIPTION OF THE INVENTION

The present invention in general relates to an improved process for producing acrylic ester comprising the steps of:

(1) oxidizing propylene or acrolein in the presence of a catalyst to obtain a reaction gas effluent stream containing an acrylic acid fraction;
(2) condensing said reaction gas stream to obtain a condensed crude acrylic acid solution;
(3) refining said condensed crude acrylic acid solution; and
(4) reacting the refined acrylic acid solution obtained according to Step (3) above with an alcohol in the presence of a catalyst to produce acrylic ester and water;

the improvement which comprises eliminating or greatly minimizing said refining Step (3) by (A) partially condensing said reaction gas stream of Step (1) above to obtain (i) a first crude liquid stream of an enriched acrylic acid solution containing about 10 to about 90% of said acrylic acid fraction and (ii) a second uncondensed reaction gas stream containing from about 90 to about 10% of said acrylic acid fraction; and
(B) without first having combined said obtained crude liquid stream of enriched acrylic acid solution with any additional crude liquid acrylic acid obtained by condensing said second uncondensed reaction gas stream defined above, and also either without having first refined said obtained crude liquid stream of enriched acrylic acid solution, or after essentially having removed only some aldehyde and/or water by-product from said obtained crude liquid stream of enriched acrylic acid solution; employing said obtained crude liquid stream of enriched acrylic acid solution as the acrylic acid starting material reactant for the esterification process of Step (4) above.

It has been found that to accomplish the partial recovery of acrylic acid from the catalytic reaction gas stream to obtain the enriched acrylic acid fraction with a significantly enhanced purity of the present invention, the condensation conditions in the first condensation stage should be maintained such that the proportion of acrylic acid which is recovered as the enriched acrylic acid ranges from about ten to about ninety percent of the total acrylic acid content (eighty percent when steam diluent is utilized) of the reaction gas stream, the water content of the recovered product (i.e., the enriched acrylic acid fraction) ranges from about five to about sixty weight percent and the formaldehyde content of the recovered product ranges from 0 to 1.0 weight percent. The preferred proportion of the recovery in the enriched acrylic acid is from about twenty to about seventy percent of the total acrylic acid when an inert diluent is employed (from about ten to about fifty percent when steam diluent is employed) with from about five to about fifty weight percent water and from about 0 to 0.7 weight percent formaldehyde; and a particularly preferred acrylic acid recovery is from about forty to about sixty percent of the total acrylic acid with from about five to about twenty weight percent water (with anhydrous diluent) and about 0 to 0.5 weight percent formaldehyde.

A quench/scrubber which has separated quenching and scrubbing sections in the same column is preferably used to partially recover a portion of the crude acid in a quench operation for use directly without further refining for the acrylate production. The incoming gases near the base of the column are quenched with the cooled wet acid product so that portion of the acrylic acid is condensed and exited through the bottom of the quench. Part of the quench tails is cooled and recycled as quench liquid. The remainder of the quench tails acid may be used directly to make acrylic esters as described in this invention.

After condensation and recovery of the acrylic acid in the first partial recovery stage to yield the enriched acrylic acid fraction, the uncondensed reaction gases including unrecovered acrylic acid vapors and various unrecovered contaminants are passed to a second stage for recovering the remainder of the acrylic acid. The second stage acrylic acid recovery may employ any conventional technique and conditions which are suitable for recovering the remaining acrylic acid from the reaction gases. In the subject invention, the previously-obtained condensed first stage recovery quench tails liquid is employed as a starting material for the production of acrylic esters without having been combined with the second stage recovery acrylic acid liquid.

In one process, a liquid which contains acrylic acid is recovered by the use of a tray inserted in the acid scrubber column. The tray has an upwardly raised section which defines an aperture through which noncondensed second stage effluent gases pass for water scrubbing. The tray thus collects falling condensed, water-scrubbed gases for removal before they can pass into the bottom of the scrubber column. Accordingly, the liquid which is condensed in the scrubber column base is not contaminated by the water-scrubbed liquids.

In the preferred quench/scrubber, the noncondensable gases together with the uncondensed products enter the scrubbing section where they are scrubbed with the incoming water near the top of the column. The liquid holding tray installed at the lower part of the scrubbing section collects the scrubbed liquid product. The liquid from this scrubbing section is pumped to the existing acid recovery system. The noncondensables exit through the top of the scrubber where they are either recycled to the reactor or sent to a combustor. The ranges of operating conditions for the scrubber/quench are listed below:

|  | Operating Range |
|---|---|
| Converter GHSV, hr-1 | 1000–4000 |
| Quench Feed P, psig | 0–30 |
| Quench Feed T., °C. | 50–350 |
| Quench Base T., °C. | 20–150 |

| | Operating Range |
|---|---|
| Quench Overhead T., °C. | 20-150 |
| Quenching Liquid T., °C. | 20-60 |
| Quench P., psig | 0-30 |

This crude acrylic acid is reacted with primary alcohols such as methanol, ethanol, butanol, isobutanol and 2-ethylhexanol to produce the corresponding acrylic esters. In particular, when the alcohol is ethanol, the resulting ester is ethyl acrylate. The esterification reaction for light esters such as ethyl acrylate is normally carried out in a reactor equipped with a product recovery distillation column whereby the crude product esters are removed at the column overhead in the form of ester/alcohol/water azeotrope. Excess alcohol is normally used in the esterification reaction, with acid such as sulfuric or sulfonic acid employed as catalyst. The ranges of operating conditions for the reaction of acrylic acid with ethanol to ethyl acrylate are listed below:

| | Operating Range | Preferred Range |
|---|---|---|
| $H_2SO_4$ Conc., wt. % | 0.3-20 | 1-5 |
| EtOH/Acrylic Acid Mole Ratio | 1:1-4:1 | 1:1-3:1 |
| LHSV, cc/Rx Liq. Vol./hr | 0.5-5.0 | 1.0-2.0 |
| Rx Kettle T., °C. | 100-150 | 110-130 |
| Reactor Pressure, mmHg | 200-1500 | 760-1050 |

The following examples are provided to further illustrate various embodiments of the present invention. The examples are intended to be illustrative in nature and thus are not to be construed as limiting the scope of the invention.

Partial Recovery Of Enriched Acrylic Acid Via Quenching

In order to demonstrate an enriched acid recovery according to the present invention, acrylic acid reaction gas mixtures were produced using steam and inert gas diluents. Apparatus and procedure for the two-stage propylene oxidation to form acrylic acid are described, for example, in co-pending U.S. Pat. application Ser. No. 281,887. When anhydrous diluents are utilized, the acrylic acid and water concentration in the reactor gas effluent produced were approximately 5-7 and 7-9 mole percent, respectively. The balance primarily was nitrogen (87-90 mole percent), oxygen (1.5-2.0 mole percent), propylene (0.3-2.5 mole percent), carbon monoxide, carbon dioxide, and other minor impurities such as acetic acid, formaldehyde, acetaldehyde and acrolein. With steam as diluent, the acrylic acid and water concentration in the reactor gas effluent were approximately 5-7 and 45-50 mole percent, respectively. The balance again was primarily nitrogen, oxygen, propylene, carbon oxides and other minor impurities.

The first stage acrylic acid recovery arrangement consisted of a stainless steel column with packed sections. The reactor gas effluent was passed to the base of the column where it was quenched by cooled wet acid produced in two consecutive quenching sections as the reaction gas proceeded up the column. The degree of partial acrylic acid condensation in the tails of the first stage recovery can routinely be selected by the technician dependent upon variables, e.g., propylene/acrolein oxidation feed rates; reaction gas temperature; quenching liquid temperatures and flow rates; quench base temperature and pressure; and the like.

Examples I-III (Table 1-3) show how the proportions of contaminants which condense in the enriched acrylic acid fraction using anhydrous diluent increases with the percentage of acrylic acid which is recovered. See, for example, the rates (weight percent times flow rate) of formaldehyde, acrolein, water and acetic acid which are obtained in Stream 2. Similar results are shown by comparing Tables 4-6 (Examples IV-VI) using steam diluent. These results illustrate that during partial acrylic acid recovery, much of the lighter impurities (e.g., acrolein, formaldehyde, acetaldehyde and the like) exit with non-condensed gases in the first stage recovery.

Preparation of Acrylic Esters

In order to demonstrate the advantages of the preferred embodiment of the present invention, refined acrylic acid (ester grade), and the crude enriched acrylic acid utilized in the subject application from an oxidation reactor using anhydrous gas diluent were each reacted with alcohol in an esterification reactor to produce acrylic ester.

Ethyl acrylate was prepared in the laboratory by reacting acrylic acid (or according to the present invention, the enriched acrylic acid) and ethanol in the presence of 3-5 percent sulfuric acid catalyst in a 500 cc 3-neck round-bottom flask equipped with a thermowell, a magnetic stirrer, a product recovery distillation column (two 1" i.d. Oldershaw columns; one 3-tray and one 10-tray), a condenser, a liquid dividing head, a product receiver and two cold traps.

In a typical laboratory experiment, 250 cc of ethyl acrylate reactor contents containing phenothiazine inhibitor (to prevent dimerization, 1-10 percent sulfuric acid (preferably 3-5 percent) and a few percent each of water, acrylic acid, ethyl acrylate and ethanol, with the remainder being heavies was charged to the kettle. The liquid feed of acrylic acid, ethanol and water (ethanol : acrylic acid mole ratio being in the range of 1:1-4:1) was fed continuously to the reactor at a feed rate of 200-500 cc/hr. The kettle temperature was about 100° C.-150° C. and the reaction was carried out at about 200 mmHg to 10 psig. By controlling the heat input and reaction temperature, the reaction product was taken at the overhead reactor column at a rate similar to the total liquid feed rate. The reactor column was operated at a reflux ratio of 0.5-2.0, and the resulting reactor overhead temperature was about 78° C.-85° C. Alternatively, the enriched acrylic acid can be fed directly to the product recovery distillation column (e.g., to the third tray of the reactor column) to remove volatile aldehydes (acrolein, formaldehyde and acetaldehyde) and water from the enriched acrylic acid before reacting with the ethanol in the kettle to produce less by-products. The trays below the steam point serve as a stripping section to remove the volatile impurities. Examples VII-X and Table 7 give the esterification results.

Examples VII-X (Table 7) show how an impurity, formaldehyde, in the enriched crude acrylic acid when directly fed to the ethyl acrylate reactor effects the ethyl acrylate crude product. The more concentrated the enriched acrylic acid or the lower the percentage of acrylic acid recovered in the quench tails (i.e., the lower the formaldehyde content in the enriched acrylic acid), the less by-product diethoxymethane is presented in the overhead ethyl acrylate crude product. Example VII is the reaction of ethanol with the normal refined (ester grade) acrylic acid, and this forms the control, or base for comparison. Examples VIII and IX are the reactions of ethanol with the enriched crude acrylic acid obtained from the vapor phase oxidation of propylene/acrolein using inert gas as diluent, and at different levels of acid recovery. Example X is the preferred mode of making ethyl acrylate using the enriched crude acrylic acid where the enriched acid is fed directly to the third tray of the reactor column to aid the removal of additional formaldehyde and water before reacting with ethanol in the kettle. Ethanol/water/sulfuric acid is fed separately to the reactor kettle.

EXAMPLE I

In a typical procedure, the gaseous reactor effluent (3,046 standard liters/hr) produced from the vapor phase oxidation of propylene with nitrogen as an inert gas diluent and containing 6.02 volume percent acrylic acid, 8.23 volume percent water, 0.18 volume percent formaldehyde, 0.17 volume percent acrolein, 0.17 volume percent acetic acid with the remainder being nitrogen, oxygen, carbon oxides and propylene, was cooled to 94° C. before feeding to a scrubber/quench system. This incoming gas was quenched with liquid product with quench liquid flow rates and quenching temperature set at 1.5 liters/hr (40° C.) and 0.75 liters/hr (30° C.). After quenching, the condensed liquid was separated from the vapors and exited through the base of the column.

The condensed liquid product obtained from quenching the oxidation effluent (i.e., the "quench tails") contained about 84.84 weight percent acrylic acid, 13.53 weight percent water, 1.53 weight percent acetic acid, 0.23 weight percent acrolein and 0.52 weight percent formaldehyde. A portion of the quench tail liquid product stream was passed through two separate heat exchangers and recycled as the quenching liquid. The remaining quench tail enriched acrylic acid (642.7 gm) was directly used as feed to the ethyl acrylate reactor (i.e., without being combined with any additional condensed liquid from the second stage) as discussed in Examples VII-X below. The amount of acrylic acid which was recovered from the reactor effluent in this enriched quench tails was calculated to be 92.5 percent.

The noncondensed vapors contain 0.50 volume percent acrylic acid, 5.28 volume percent water, 0.12 volume percent acrolein, 0.05 volume percent formaldehyde with the remainder being nitrogen, oxygen, carbon oxides and propylene, and were exited through the quenched section to the second stage acrylic acid recovery at 45° C. and 2,766 standard liters/hr. These noncondensed vapors, when recovered as liquid in the second stage acrylic acid recovery were not mixed with the enriched acrylic acid quench tail solution. The results are given in Table 1.

EXAMPLE II

Example I was repeated in which the incoming quench feed was cooled to 188° C. In addition, each of the incoming quench liquid flow rate and quenching temperatures at the quench section were respectively set at 0.75 liters/hr and 30° C. 486.9 gm of the enriched product containing 91.63 weight percent acrylic acid, 6.37 weight percent water, 1.71 weight percent acetic acid, 0.06 weight percent acrolein and 0.03 weight percent formaldehyde was obtained at the quench tails.

The noncondensed vapors having 1.56 volume percent of acrylic acid, 7.32 volume percent water, 0.04 volume percent acetic acid, 0.08 volume percent acrolein, 0.08 percent formaldehyde with the remainder being nitrogen, oxygen, carbon oxides and propylene were exited through the quench section to the second stage acrylic acid recovery at 45° C. and 2,861 standard liters/hr. The amount of acrylic acid which was recovered in the enriched quenched tails was calculated to be 75.7 percent. The results are given in Table 2.

EXAMPLE III

The same as in Example I except that the incoming quench feed was cooled to 189° C. and fed at 4,005 standard liters/hr. The incoming vapors from the reactor effluent contained 5.49 volume percent acrylic acid, 6.74 volume percent water, 0.21 volume percent acetic acid, 0.04 volume percent acrolein, 0.13 volume percent formaldehyde with the remainder being nitrogen, oxygen, propylene and carbon oxides. In addition, the quench liquid feed rates and quenching temperatures at the quench section were set at 1.0 liter/hr (63° C.) and 1.0 liters/hr (50° C.). 427.2 gm of enriched product containing 89.82 weight percent acrylic acid, 8.22 weight percent water, 1.72 weight percent acetic acid and 0.14 weight percent formaldehyde was obtained at the quench tails.

3,748 standard liters/hr of the noncondensed gas having a composition of 2.55 volume percent acrylic acid, 5.87 volume percent water, 0.15 volume percent acetic acid, 0.12 volume percent acrolein and 0.12 volume percent formaldehyde was exited through the quench section to the second state acrylic acid recovery at 65° C. The amount of acrylic acid which was recovered in the enriched quenched tails was calcuated to be 55.5 percent. The results are given in Table 3.

EXAMPLES IV-VI

Steam was used as diluent for the vapor phase propylene/acrolein oxidation instead of an inert gas. The same recovery procedure as described in Examples I- III was employed. In Example IV, after the recovery of the first liquid stream of the tails of enriched acrylic acid, the second stage noncondensed vapors from the first stage recovery was further condensed in a 5. separate heat exchanger to recover all the acrylic acid in a liquid stream which was combined with the first liquid stream. In Examples V and VI, the same partial recovery prodcedures as Examples II and III were employed. In Examples IV-VI, the amount of acrylic acid which was recovered in the enriched quenched tails was calculated to be 100, 73.9 and 66.1 percent, respectively. The conditions utilized and results are given in Tables 4-6.

EXAMPLE VII

Ethyl acrylate was prepared in the laboratory using the apparatus described in the preparation of acrylic ester section. The feed solution was pre-mixed with 916 gm anhydrous ethanol, 622.5 gm acrylic acid (conventionally extensively refined; greater than 99.5% purity) and 69.6 gm distilled water before feeding to the ethyl acrylate reactor which contained 250 cc of ethyl acrylate stock solution. Crude product was taken at the reactor column overhead at a rate similar to the liquid feed rate by controlling the amount of heat input. A reflux ratio of 0.8 was maintained at the reactor column. The reaction was continued for about 6 hours and the reactor overhead crude product was taken periodically for analysis. The results and the reaction conditions are given in Table 7. This forms the control base used for comparison when crude enriched acrylic acid is used as feed to the ethyl acrylate reactor.

EXAMPLE VIII

Example VII was repeated in which the ethyl acrylate feed was obtained by pre-mixing 1175 gm anhydrous ethanol, 1000 gm crude enriched acrylic acid obtained from Example I and 88 gm distilled water. At the end of the run, a slight build-up in reactor volume was observed. The results are given in Table 7.

EXAMPLE IX

Example VII was repeated in which the ethyl acrylate feed was obtained by pre-mixing 848 gm anhydrous ethanol, 620 gm crude enriched acrylic acid obtained from Example III and 64 gm distilled water. A slight build-up in reactor volume was observed at the end of the run. The results are given in Table 7.

EXAMPLE X

Example VII was repeated except that a partially condensed crude enriched acid obtained as in Examples I—III and containing 89.7 weight percent acrylic acid, 1.1 weight percent acetic acid, 5.4 weight percent water, 0.12 weight percent formaldehyde and 3.68 weight percent heavies, i.e., other components heavier than acrylic acid, was fed directly to tray 3 of a 13-tray Oldershaw column (the 3 and 10-tray columns described above) to aid the removal of some light components (e.g., formaldehyde) and water by distillation before reacting with the ethanol in the reactor kettle. A mixture of ethanol (97.3 weight percent), water (2.5 weight percent) and sulfuric acid (0.2 weight percent) was fed separately to the reactor kettle. A reactor kettle volume of 330 cc and a reflux ratio of 1.5 were maintained for this run. Reaction product was taken overhead and a continuous reactor purge was used to remove the heavies from the reactor. The reaction was continued for a total of 95 hours. The results and the reaction conditions are given in Table 7.

TABLE 1

ENRICHED ACRYLIC ACID
92.5% RECOVERY
ANHYDROUS DILUENT

Stream Compositions

| Components | Stream 1 Mole % | Stream 2 Weight % | Stream 3 Mole % | Stream 4 Weight % |
|---|---|---|---|---|
| Acrolein | 0.17 | 0.23 | 0.12 | — |
| Formaldehyde | 0.18 | 0.52 | 0.05 | — |
| Water | 8.23 | 13.53 | 5.28 | 95.00 |
| Acetic Acid | 0.17 | 1.53 | — | — |
| Acrylic Acid | 6.02 | 84.84 | 0.50 | — |
| Hydroquinone | — | — | — | 5.00 |
| Other gases[1] | 85.23 | — | 94.43 | — |
| Flow Rates[2] | 3,046 | 642.7 | 2,766 | 40.00 |
| Temperature, °C. | 94 | 65 | 45 | Ambient |
| Quench Flow 1[3] | | 1.5 | | |
| Quench Temp. 1, °C. | | 40 | | |
| Quench Flow 2[3] | | 0.75 | | |
| Quench Temp. 2, °C. | | 30 | | |
| Quench Pressure psig | | 6.5 | | |

TABLE 1-continued

ENRICHED ACRYLIC ACID
92.5% RECOVERY
ANHYDROUS DILUENT

Stream Compositions

| Components | Stream 1 Mole % | Stream 2 Weight % | Stream 3 Mole % | Stream 4 Weight % |
|---|---|---|---|---|

Notes:
[1]Other gases include nitrogen, oxygen, propylene, carbon monoxide, carbon dioxide, etc.
[2]Flow rates, standard liter/hr for gas stream and gm/hr for liquid stream.
[3]Quench flow rate in liter/hr.
Stream 1 = Reactor effluent, feed to first stage acrylic acid recovery.
Stream 2 = Partially recovered enriched acrylic acid suitable for esterification.
Stream 3 = To second recovery stage before further refining.
Stream 4 = Phenothiazine inhibitor feed.

TABLE 2

ENRICHED ACRYLIC ACID
75.7% RECOVERY
ANHYDROUS DILUENT

Stream Compositions

| Components | Stream 1 Mole % | Stream 2 Weight % | Stream 3 Mole % | Stream 4 Weight % |
|---|---|---|---|---|
| Acrolein | 0.17 | 0.06 | 0.08 | — |
| Formaldehyde | 0.18 | 0.03 | 0.08 | — |
| Water | 8.23 | 6.37 | 7.32 | 95.00 |
| Acetic Acid | 0.17 | 1.71 | 0.04 | — |
| Acrylic Acid | 6.02 | 91.63 | 1.56 | — |
| Hydroquinone | — | — | — | 5.00 |
| Other gases[1] | 85.23 | — | 94.43 | — |
| Flow Rates[2] | 3,046 | 486.9 | 2,861 | 40.00 |
| Temperature, °C. | 188 | 80 | 60 | Ambient |
| Quench Flow 1[3] | | 0.75 | | |
| Quench Temp. 1, °C. | | 30 | | |
| Quench Flow 2[3] | | 0.75 | | |
| Quench Temp. 2, °C. | | 30 | | |
| Quench Pressure psig | | 6.8 | | |

Notes:
[1]Other gases include nitrogen, oxygen, propylene, carbon monoxide, carbon dioxide, etc.
[2]Flow rates, standard liter/hr for gas stream and gm/hr for liquid stream.
[3]Quench flow rate in liter/hr.
Stream 1 = Reactor effluent, feed to first stage acrylic acid recovery.
Stream 2 = Parially recovered enriched acrylic acid suitable for esterification.
Stream 3 = To second recovery stage before further refining.
Stream 4 = Phenothiazine inhibitor feed.

TABLE 3

ENRICHED ACRYLIC ACID
55.5% RECOVERY
ANHYDROUS DILUENT

Stream Compositions

| Components | Stream 1 Mole % | Stream 2 Weight % | Stream 3 Mole % | Stream 4 Weight % |
|---|---|---|---|---|
| Acrolein | 0.04 | — | 0.12 | — |
| Formaldehyde | 0.13 | 0.14 | 0.12 | — |
| Water | 6.74 | 8.22 | 5.87 | 95.00 |
| Acetic Acid | 0.21 | 1.71 | 0.15 | — |
| Acrylic Acid | 5.49 | 89.92 | 2.55 | — |
| Hydroquinone | — | — | — | 5.00 |
| Other gases | 87.39 | — | 91.19 | — |
| Flow Rates[2] | 4,005 | 427.2 | 3,748 | 40.00 |
| Temperature, °C. | 189 | 71 | 65 | Ambient |
| Quench Flow 1[3] | | 1.0 | | |
| Quench Temp. 1, °C. | | 64 | | |
| Quench Flow 2[3] | | 1.0 | | |
| Quench Temp. 2, °C. | | 36 | | |
| Quench Pressure | | 9.9 | | |

TABLE 3-continued

ENRICHED ACRYLIC ACID
55.5% RECOVERY
ANHYDROUS DILUENT

Stream Compositions

| Components | Stream 1 Mole % | Stream 2 Weight % | Stream 3 Mole % | Stream 4 Weight % |
|---|---|---|---|---|
| psig | | | | |

Notes:
[1] Other gases include nitrogen, oxygen, propylene, carbon monxide, carbon dioxide, etc.
[2] Flow rates, standard liter/hr for gas stream and gm/hr for liquid stream.
[3] Quench flow rate in liter/hr.
Stream 1 = Reactor effluent, feed to first stage acrylic acid recovery.
Stream 2 = Partially recovered enriched acrylic acid suitable for esterification.
Stream 3 = To second recovery stage before further refining.
Stream 4 = Phenothiazine inhibitor feed.

TABLE 4

COMPLETE ACRYLIC ACID RECOVERY
STEAM DILUENT

Stream Compositions

| Components | Stream 1 Mole % | Stream 2 Weight % | Stream 3 Mole % | Stream 4 Weight % |
|---|---|---|---|---|
| Acrolein | 0.73 | 0.55 | 1.10 | — |
| Formaldehyde | 0.15 | 0.15 | 0.17 | — |
| Water | 48.08 | 63.22 | 18.16 | 95.00 |
| Acetic Acid | 0.26 | 1.28 | 0.04 | — |
| Acrylic Acid | 5.40 | 34.62 | — | — |
| Hydroquinone | — | 0.11 | — | 5.00 |
| Other gases[1] | 45.38 | — | 80.53 | — |
| Flow Rates[2] | 3,912 | 1,961 | 2,202 | 52 |
| Temperature, °C. | 173 | 89 | 19 | Ambient |
| Quench Flow 1[3] | | 1.125 | | |
| Quench Temp. 1, °C. | | 31 | | |
| Quench Flow 2[3] | 1.125 | | | |
| Quench Temp. 2, °C. | | 38 | | |
| Quench Pressure psig | | 4.5 | | |

Notes:
[1] Other gases include nitrogen, oxygen, propylene, carbon monoxide, carbon dioxide, etc.
[2] Flow rates, standard liter/hr for gas stream and gm/hr for liquid stream.
[3] Quench flow rate in liter/hr.
Stream 1 = Reactor effluent, feed to first stage acrylic acid recovery.
Stream 2 = Complete recovery of acrylic acid by addition of indirect cooling.
Stream 3 = Off-gas to sodium bisulfite scrubber.
Stream 4 = Phenothiazine inhibitor feed.

TABLE 5

ENRICHED ACRYLIC ACID
73.9% RECOVERY
STEAM DILUENT

Stream Compositions

| Components | Stream 1 Mole % | Stream 2 Weight % | Stream 3 Mole % | Stream 4 Weight % |
|---|---|---|---|---|
| Acrolein | 0.35 | — | 0.48 | — |
| Formaldehyde | 0.18 | 0.12 | 0.21 | — |
| Water | 44.78 | 58.41 | 30.55 | 95.00 |
| Acetic Acid | 0.31 | 1.81 | 0.13 | — |
| Acrylic Acid | 5.44 | 39.37 | 1.94 | — |
| Hydroquinone | — | 0.20 | — | 5.00 |
| Other gases[1] | 48.94 | — | 66.69 | — |
| Flow Rates[2] | 3,194 | 1,049 | 2,343 | 40.00 |
| Temperature, °C. | 151 | 91 | 81 | Ambient |
| Quench Flow 1[3] | | 1.125 | | |
| Quench Temp. 1, °C. | | 15 | | |
| Quench Flow 2[3] | | 1.125 | | |
| Quench Temp. 2, °C. | | 32 | | |
| Quench Pressure psig | | 5.3 | | |

TABLE 5-continued

ENRICHED ACRYLIC ACID
73.9% RECOVERY
STEAM DILUENT

Stream Compostions

| Components | Stream 1 Mole % | Stream 2 Weight % | Stream 3 Mole % | Stream 4 Weight % |
|---|---|---|---|---|
| psig | | | | |

Notes:
[1] Other gases include nitrogen, oxygen, propylene, carbon monoxide, carbon dioxide, etc.
[2] Flow rates, standard liter/hr for gas stream and gm/hr for liquid stream.
[3] Quench flow rate in liter/hr.
Stream 1 = Reactor effluent, feed to first stage acrylic acid recovery.
Stream 2 = Partially recovered enriched acrylic acid suitable for esterification.
Stream 3 = To second recovery stage before further refining.
Stream 4 = Phenothiazine inhibitor feed.

TABLE 6

ENRICHED ACRYLIC ACID
66.1% RECOVERY
STEAM DILUENT

Stream Compostions

| Components | Stream 1 Mole % | Stream 2 Weight % | Stream 3 Mole % | Stream 4 Weight % |
|---|---|---|---|---|
| Acrolein | 0.73 | 0.23 | 0.48 | — |
| Formaldehyde | 0.15 | 0.11 | 0.21 | — |
| Water | 48.08 | 47.38 | 30.55 | 95.00 |
| Acetic Acid | 0.26 | 1.83 | 0.13 | — |
| Acrylic Acid | 5.40 | 50.31 | 1.94 | — |
| Hydroquinone | — | 0.02 | — | 5.00 |
| Other gases[1] | 45.38 | — | 66.69 | — |
| Flow Rates[2] | 3,912 | 892 | 3,284 | 40.00 |
| Temperature, °C. | 173 | 89 | 78 | Ambient |
| Quench Flow 1[3] | | 1.125 | | |
| Quench Temp. 1, °C. | | 31 | | |
| Quench Flow 2[3] | | 1.125 | | |
| Quench Temp. 2, °C. | | 38 | | |
| Quench Pressure psig | | 4.5 | | |

Notes:
[1] Other gases include nitrogen, oxygen, propylene, carbon monoxide, carbon dioxide, etc.
[2] Flow rates, standard liter/hr for gas stream and gm/hr for liquid stream.
[3] Quench flow rate in liter/hr.
Stream 1 = Reactor effluent, feed to first stage acrylic acid recovery.
Stream 2 = Partially recovered enriched acrylic acid suitable for esterification.
Stream 3 = To second recovery stage before further refining.
Stream 4 = Phenothiazine inhibitor feed.

TABLE 7

ETHYL ACRYLATE PRODUCTION

| | Ex. VII | Ex. VIII | Ex. IX | Ex. X |
|---|---|---|---|---|
| Conditions | | | | |
| Reflux Ratio | 0.8 | 0.8 | 0.8 | 1.5 |
| Overhead T., °C. | 79 | 78 | 81 | 81 |
| Kettle T., °C. | 116 | 101 | 115 | 121.5 |
| Reactor P., mmHg | 760 | 760 | 760 | 760 |
| Tray 3 T., °C. | — | — | — | 93 |
| EtOH/AA Mole Ratio | 2.33 | 2.14 | 2.45 | 2.10 |
| Liquid Feed Rate, cc/hr | 273 | 284 | 278 | — |
| AA Feed to Tray 3, cc/hr | — | — | — | 159.4 |
| EtOH/H2O/H2SO4 Feed, cc/hr | — | — | — | 236.6 |
| Reactor Production Rate, cc/hr | 273 | 281 | 276 | 355 |
| Reactor Purgte Rate, cc/hr | — | — | — | 21.5 |
| Product, Wt. % | | | | |
| Ethanol (EtOH) | 34.31 | 33.72 | 33.93 | 24.4 |
| Water | 14.42 | 13.46 | 15.17 | 15.0 |
| Ethyl Acetate | 0.043 | 0.946 | 1.166 | 1.500 |
| Diethoxymethane | — | 0.328 | 0.021 | 0.015 |
| Ethyl Acrylate | 50.43 | 50.11 | 48.06 | 58.3 |
| Acrylic Acid (AA) | — | — | — | 0.20 |
| Others | 0.80 | 1.44 | 1.65 | 0.565 |

The present invention is therefore directed towards the recovery of a crude liquid stream of enriched acrylic acid and its use in a catalytic esterification reactor without undergoing the conventional extensive refining steps previously mentioned. However, minor purification may be optionally performed on the crude liquid stream of enriched acrylic acid essentially to remove aldehydes or water therefrom if desired. As mentioned above, minimizing the water content of the crude liquid stream of enriched acrylic acid enhances the completion of the esterification reaction and minimizing the aldehydes in the crude liquid stream of enriched acrylic acid precludes the formation of the previously-discussed build-up in the ester reactor. In this regard, lighter aldehydes, especially formaldehyde, can be quite simply removed before the crude liquid stream of enriched acrylic acid is esterified by feeding such stream to the product recovery distillation column of the esterification reactor kettle. The heat from the gaseous esterification reactor effluent is thus utilized to distill much of the fraction of lighter aldehydes before the crude enriched acrylic acid liquid stream enters the reactor kettle. Similarly, water can be removed in the same manner. Alternatively, of course, aldehydes (including heavier aldehydes) and water may be conventionally removed by distillation in any suitable vessel prior to feeding the enriched acrylic acid liquid stream directly to the esterification reactor.

It should be understood that various modifications can be made to the preferred embodiments disclosed herein without departing from the spirit and scope of the invention or without the loss of its attendant advantages. Thus, other examples applying the principles described herein are intended to fall within the scope of the invention provided the features stated in any of the following claims or the equivalent of such be employed.

We claim:

1. In a process for producing acrylic ester comprising the steps of:
   (1) oxidizing propylene or acrolein in the presence of a catalyst to obtain a reaction gas effluent stream containing an acrylic acid fraction;
   (2) condensing said reaction gas stream to obtain a condensed crude acrylic acid solution;
   (3) refining said condensed crude acrylic acid solution; and
   (4) reacting the refined acrylic acid solution obtained according to Step (3) above with an alcohol in the presence of a catalyst to produce acrylic ester and water;
   the improvement which comprises eliminating or greatly minimizing said refining Step (3) by
   (A) partially condensing said reaction gas stream of Step (1) above to obtain (i) a first crude liquid stream of an enriched acrylic acid solution containing about 10 to about 90% of said acrylic acid fraction and (ii) a second uncondensed reaction gas stream containing from about 90 to about 10% of said acrylic acid fraction; and
   (B) without first having combined said obtained crude liquid stream of enriched acrylic acid solution with any additional crude liquid acrylic acid obtained by condensing said second uncondensed reaction gas stream defined above, and also either without having first refined said obtained crude liquid stream of enriched acrylic acid solution, or after essentially having removed only some aldehyde and/or water byproduct from said obtained crude liquid stream of enriched acrylic acid solution; employing said obtained crude liquid stream of enriched acrylic acid solution as the acrylic acid starting material reactant for the esterification process of Step (4) above.

2. The process for producing acrylic ester according to claim 1, wherein said Step (1) utilizes an anhydrous diluent.

3. The process for producing acrylic ester according to claim 2, wherein said first crude liquid stream of enriched acrylic acid solution obtained from Step (A) contains from about 10 to about 80% of said acrylic acid fraction.

4. The process for producing acrylic ester according to claim 1, wherein said first crude liquid stream of enriched acrylic acid solution contains from about 5 to about 60 weight percent water.

5. The process for producing acrylic ester according to claim 4, wherein said Step (1) utilizes steam diluent and said first crude liquid stream of enriched acrylic acid solution obtained from Step (A) contains from about 10 to about 50% of said acrylic acid fraction.

6. The process for producing acrylic ester according to claim 3, wherein said crude liquid stream of enriched acrylic acid solution contains from about 20 to about 70 percent of said acrylic acid fraction.

7. The process for producing acrylic ester according to claims 5 or 6, wherein said first crude liquid stream of enriched acrylic acid solution contains from about 5 to about 50 weight percent water.

8. The process for producing acrylic ester according to claims 6, wherein said crude liquid stream of enriched acrylic acid solution contains from about 40 to about 70 percent of said acrylic acid fraction.

9. The process for producing acrylic ester according to claim 8, wherein said first crude liquid stream of enriched acrylic acid solution contains from about 5 to about 20 weight percent water.

10. The process for producing acrylic ester according to any of claims 1–4, wherein aldehyde is removed from said crude liquid stream of enriched acrylic acid solution before said esterification with alcohol.

11. The process for producing acrylic ester according to claim 10, wherein said aldehyde is formaldehyde.

12. The process for producing acrylic ester according to claim 11, wherein said formaldehyde is removed by feeding said crude liquid stream of enriched acrylic acid solution to an esterification reactor via a product recovery distillation column thereof.

13. The process for producing acrylic ester according to claim 10, wherein said crude liquid stream of acrylic acid solution contains from 0 to 1.0 wt. percent formaldehyde.

14. The process for producing acrylic ester according to claim 13, wherein said crude liquid stream of enriched acrylic acid solution contains from 0 to 0.7 wt. % formaldehyde.

15. The process for producing acrylic ester according to claim 14, wherein said crude liquid stream of enriched acrylic acid solution contains from 0 to 0.5 wt. % formaldehyde.

* * * * *